(12) United States Patent
Spiegel et al.

(10) Patent No.: US 9,622,469 B2
(45) Date of Patent: Apr. 18, 2017

(54) CROSSLINK BREAKERS FOR PRESERVATION OF BIOLOGICAL SUBSTANCES

(71) Applicants: David Spiegel, New Haven, CT (US); Jeanne Hendrickson, New Haven, CT (US)

(72) Inventors: David Spiegel, New Haven, CT (US); Jeanne Hendrickson, New Haven, CT (US)

(*) Notice: Subject to any disclaimer, the term of this patent is extended or adjusted under 35 U.S.C. 154(b) by 197 days.

(21) Appl. No.: 14/505,992

(22) Filed: Oct. 3, 2014

(65) Prior Publication Data
US 2015/0099260 A1 Apr. 9, 2015

Related U.S. Application Data

(60) Provisional application No. 61/886,209, filed on Oct. 3, 2013.

(51) Int. Cl.
*A01N 1/02* (2006.01)

(52) U.S. Cl.
CPC .................. *A01N 1/0226* (2013.01)

(58) Field of Classification Search
CPC .................................................. A01N 1/0226
See application file for complete search history.

(56) References Cited

U.S. PATENT DOCUMENTS

| | | | |
|---|---|---|---|
| 5,853,703 | A | 12/1998 | Cerami et al. |
| 8,709,707 | B2 | 4/2014 | Hess et al. |
| 2005/0233302 | A1 | 10/2005 | Hess et al. |
| 2007/0025926 | A1 | 2/2007 | Cerami et al. |
| 2009/0124674 | A1 | 5/2009 | Egan et al. |

FOREIGN PATENT DOCUMENTS

EP 1248615 B1 5/2007

OTHER PUBLICATIONS

Wang et al. (Transfusion (Sep. 1, 2013) 53: 88A; presented at the AABB Annual Meeting and CTTXPO, Denver CO, Oct. 10-15, 2013.*
Foiles et al. Expert Opinion Invest. Drugs (2001) 10(11): 1977-1987.*
F. M. Pieracci et al., The Age of Transfused Blood Predicts Hematocrit Response Among Critically Ill Surgical Patients, The American Journal of Surgery, Sep. 2012, pp. 269-273, vol. 204 No. 3, USA.
R. L. Sparrow, Time to Revisit Red Blood Cell Additive Solutions and Storage Conditions: A Role for "Omics" Analyses, Blood Transfusion, May 2012, pp. s7-s11, vol. 10 (Suppl 2), USA.
J. E. Hendrickson et al., Transfusion of Fresh Murine Red Blood Cells Reverses Adverse Effects of Older Stored Red Blood Cells, Transfusion, Dec. 2011, pp. 2695-2702, vol. 51, USA.

W.C. Little et al., The Effect of Alagebrium Chloride (ALT-711), a Novel Glucose Cross-Link Breaker, in the Treatment of Elderly Patients with Diastolic Heart Failure, Journal of Cardiac Failure, Apr. 2005, pp. 191-195, vol. 11 No. 3, USA.
J. A. Weinberg, et al., Age of Transfused Blood: An Independent Predictor of Mortality Despite Universal Leukoreduction, The Journal of Trauma, Injury, Infection, and Critical Care, Aug. 2008, pp. 279-284, vol. 65 No. 2, USA.
T. Kim et al., The Unique Reactivity of N-Phenacyl-Derived Thiazolium Salts Toward Alpha-Dicarbonyl Compounds, Rejuvenation Research, 2013, pp. 43-50, vol. 16 No. 1, USA.
S. J. Cho et al., The Road to Advanced Glycation End Products: A Mechanistic Perspective, Current Medicinal Chemistry, 2007, pp. 1653-1671, vol. 14 No. 15, Canada.
S. Vasan et al., Therapeutic Potential of Breakers of Advanced Glycation End Product-Protein Crosslinks, Archives of Biochemistry and Biophysics, 2003, pp. 89-96, vol. 419, USA.
D.M. Stern et al., Receptor for Advanced Glycation Endproducts (RAGE) and the Complications of Diabetes, Ageing Research Reviews, 2002, pp. 1-15, vol. 1, USA.
M. A. Smith et al., Advanced Maillard Reaction End Products are Associated with Alzheimer Disease Pathology, Neurobiology, Proceedings of the National Academy of Sciences, Jun. 1994, pp. 5710-5714, vol. 91, USA.

(Continued)

*Primary Examiner* — Susan Hanley
(74) *Attorney, Agent, or Firm* — Carmody Torrance Sandak & Hennessey LLP (57) ABSTRACT

A preservative for body fluids, proteins, cells and tissues comprising an effective amount of an AGE crosslink breaker for preventing formation of advanced glycation end products. The AGE crosslink breaker comprises a compound of Structure (1):

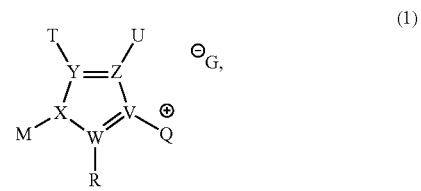

(1)

wherein V, W, X, Y and Z are any atom suitable for a heterocyclic carbene or carbene precursor framework, including B, C, O, N, S, Se, P, and As in any chemically-feasible oxidation state;

wherein Q, R, M, T and U are any atom or substituent, including but not limited to, H, $CL_n$, $NL_n$, $PL_n$, $OL_n$, $SL_n$, $SeL_n$, $L_nCl$, $L_nBr$, $L_nI$, wherein L is any atom, substituent or group, and n is any integer such that Q, R, M, T, and U can access all chemically-feasible oxidation states; and wherein G comprises any charged counter ion including, but not limited to those derived from C, O, N, B, Al, S, Se, Cl, Br, I in any chemically-feasible oxidation state.

11 Claims, 5 Drawing Sheets

(56) References Cited

OTHER PUBLICATIONS

Y. Yamamoto et al., Advanced Glycation Endproducts- Receptor Interactions Stimulate the Growth of Human Pancreatic Cancer Cells Through the Induction of Platelet-Derived Growth Factor-B, Biochemical and Biophysical Research Communications, 1996, pp. 700-705, vol. 222 No. 3, USA.

S. Vasan et al., An Agent Cleaving Glucose-Derived Protein Crosslinks In Vitro and In Vivo, Letters to Nature, Jul. 1996, pp. 275-278, vol. 382, USA.

M. Peppa et al., Prevention and Reversal of Diabetic Nephropathy in db/db Mice Treated with Alagebrium (ALT-711), American Journal of Nephrology, 2006, pp. 430-436, vol. 26, USA.

M. Asif et al., An Advanced Glycation Endproduct Cross-Link Breaker can Reverse Age-Related Increases in Myocardial Stiffness, Proceedings of the National Academy of Sciences, Mar. 2000, pp. 2809-2813, vol. 97 No. 6, USA.

B. H. R. Wolffenbuttel et al, Breakers of Advanced Glycation End Products Restore Large Artery Properties in Experimental Diabetes, Proceedings of the National Academy of Sciences, Apr. 1998, pp. 4630-4634, vol. 95, USA.

P. V. Vaitkevicius et al., A Cross-Link Breaker has Sustained Effects on Arterial and Ventricular Properties in Older Rhesus Monkeys, Proceedings of the National Academy of Sciences, Jan. 2001, pp. 1171-1175, vol. 98 No. 3, USA.

Guest Editorial, Intervention Against the Maillard Reaction In Vivo, Archives of Biochemistry and Biophysics, 2003, pp. 1-15, vol. 419, USA.

F. Turgut et al., Potential New Therapeutic Agents for Diabetic Kidney Disease, American Journal of Kidney Diseases, May 2010, pp. 928-940, vol. 55 No. 5, USA.

A. D. N. J. De Grey, Foreseeable Pharmeceutical Repair of Age-Related Extracellular Damgage, Current Drug Targets, 2006, pp. 1469-1477, vol. 7 No. 11, USA.

S. Yang et al., Age-Breakers Cleave Model Compounds, but do not Break Maillard Crosslinks in Skin and Tail Collagen from Diabetic Rats, Archives of Biochemistry and Biophysics, 2003, pp. 42-46, vol. 412, USA.

D. L. Price et al., Chelating Activity of Advanced Glycation End-Product Inhibitors, The Journal of Biological Chemistry, 2001, pp. 48967-48972, vol. 276 No. 52, USA.

P. J. Thornalley et al., Rapid Hydrolysis and Slow alpha, beta-Dicarbonyl Cleavage of an Agent Proposed to Cleave Glucose-Derived Protein Cross-Links, 1999, pp. 303-307, vol. 57, USA.

K. M. Biemel et al., Site-Specific Quantitative Evaluation of the Protein Glycation Product N6-(2,3-Dihydroxy-5,6-dioxohexyl)-L-Lysinate by LC-(ESI) MS Peptide Mapping: Evidence for Its Key Role in AGE Formation, Bioconjugate Chemistry, 2003, pp. 619-628, vol. 14 No. 3, USA.

G. Cheng et al., C16, a Novel Advanced Glycation Endproduct Breaker, Restores Cardio-Vascular Dysfunction in Experimental Diabetic Rats, Acta Pharmacologica Sinica, Dec. 2005, pp. 1460-1466, vol. 26 No. 12, USA.

G. Cheng et al., Beneficial Effects of C36, a Novel Breaker of Advanced Glycation Endproducts Cross-Links, on the Cardiovascular System of Diabetic Rats, British Journal of Pharmacology, 2007, pp. 1196-12-06, vol. 152, USA.

P. Pathak et al., TRC4149 a Novel Advanced Glycation End Product Breaker Improves Hemodynamic Status in Diabetic Spontaneously Hypertensive Rats, European Journal of Medical Research, Aug. 2008, pp. 388-398, vol. 13, USA.

D. Joshi et al., TRC4186, a Novel Age-breaker, Improves Diabetic Cardiomyopathy and Nephropathy in Ob-ZSF1 Model of Type 2 Diabetes, Journal of Cardiovascular Pharmacology, Jul. 2009, pp. 72-81, vol. 54 No. 1, USA.

S. K. Grandhee et al., Mechanism of Formation of the Maillard Protein Cross-link Pentosidine—Glucose, Fructose, and Ascorbate as Pentosidine Precursors, The Journal of Biological Chemistry, Jun. 1991, pp. 11649-11653, vol. 266 No. 18, USA.

K. Yu-Kin Chow et al., Catalytic Generation of Activated Carboxylates: Direct, Stereoselective Synthesis of beta-Hydroxyesters from Epoxyaldehydes, Journal of American Chemical Society, 2004, pp. 8126-8127, vol. 126 No. 26, USA.

M. Fukui et al., Liquid Crystal Formation in Binary Systems IV. Induction of Smectic Phases in Mixtures of N-(p-Nitrobenzylidene)-p-aminoazobenzene and Various Electron Donors of the Type N-(p-Substituted Benzylidene)-p-aminoazobenzene, The Bulletin of the Chemical Society of Japan, Oct. 1981, pp. 3137-3142, vol. 54 No. 10, USA.

T. Iwamura et al., Reinvestigation of Reactions of Thiazolium and Benzothiazolium N-phenacylides with Electron-Deficient Acetylenes, Perkin 1, Jan. 1996, paper 5/06267E, USA.

F. Heaney et al., Bridgehead Nitrogen Heterocycles which contain the Quinazoline Moiety—Synthesis and Cycloaddition of 1,2-Dihydroquinazoline 3-Oxides, Organic and Biomolecular Chemistry, 2005, pp. 4351-4361, vol. 3, USA.

O. Bortolini et al., alpha-Diketones as Acyl Anion Equivalents: A Non-Enzymatic Thiamine-Promoted Route to Aldehyde alpha-Ketone Coupling in PEG400 as Recyclable Medium, Tetrahedron, 2011, pp. 8110-8115, vol. 67, USA.

O. Bortolini et al., Thiazolium-Catalyzed Intermolecular Stetter Reaction of Linear and Cyclic Alkyl alpha-Diketones, Organic and Biomolecular Chemistry, 2011, pp. 8437-8444, vol. 9, USA.

D. S. Kemp et al., Base Catalysis of Thiazolium Salt Hydrogen Exchange and Its Implications for Enzymatic Thiamine Cofactor Catalysis, Journal of the American Chemical Society, Apr. 1970, pp. 2554-2555, vol. 92 No. 8, USA.

M. A. Schroeder et al., The Relation Between Structure and Reactivity in Five-Membered Heteroaromatic Compounds-II—CNDO/2 Calculations on Azolium Cations and on the Zwitterions Resulting from their Deprotonation, Tetrahedron, 1973, pp. 3469-3489, vol. 29, Great Britain.

J. H. Teles et al., Benzoin-Type Condensations of Formaldehyde Catalyzed by Stable Carbenes, Helvetica Chimica Acta, 1996, pp. 61-83, vol. 79, USA.

C. Fischer et al., Umpolung of Michael Acceptors Catalyzed by N-Heterocyclic Carbenes, Journal of the American Chemical Society, Feb. 2006, pp. 1472-1473, vol. 128 No. 5, USA.

J. E. Baldwin et al., Competing [1,3]- and [3,3]-Sigmatropic Rearrangements of Electron-Rich Olefins, Journal of the American Chemical Society, Jan. 1974, pp. 596-597, vol. 96 No. 2, USA.

V. Bertolasi et al., Unexpected Reactivity of Diaryl alpha-diketones with Thiazolium Carbenes: Discovery of a Novel Multicomponent Reaction for the Facile Synthesis of 1,4-thiazin-3-ones, Organic and Biomolecular Chemistry, 2012, pp. 6579-6586, vol. 10, USA.

G.P. Ferguson et al., Detoxification of Methylglyoxal by the Nucleophilic Bidentate, Phenylacylthiazolium Bromide, Chemical Research in Toxicology, 1999, pp. 617-622, vol. 12, USA.

X. Wang et al., Attenuation of Hypertension Development by Scavenging Methylglyoxal in Fructose-Treated Rats, Journal of Hypertension, 2008, pp. 765-772, vol. 26, USA.

H. Wang et al., Proinflammatory and Proapoptotic Effects of Methylglyoxal on Neutrophils from Patients with Type 2 Diabetes Mellitus, Clinical Biochemistry, 2007, pp. 1232-1239, vol. 40, USA.

A. Dhar et al., Alagebrium Attenuates Acute Methylglyoxal-Induced Glucose Intolerance in Sprague-Dawley Rats, British Journal of Pharmacology, 2010, pp. 166-175, vol. 159, Online Dec. 2009.

N. S. Mangalmurti et al., Advanced Glycation End Products on Stored Red Blood Cells Increase Endothelial Reactive Oxygen Species Generation Through Interaction with Receptor for Advance Glycation End Products, Transfusion, 2010, pp. 1-9, USA.

N. S. Mangalmurti et al., The Receptor for Advanced Glycation End Products Mediates Lung Endothelial Activation by RBCs, Dec. 2012, American Journal of Physiol Lung Cell Mol Physiol, Dec. 2012, USA.

L. Lysenko et al., The Effect of Packed Red Blood Cell Storage on Arachidonic Acid and Advanced Glycation End-Product Formation, Arch. Immunol. Ther. Exp., 2006, pp. 357-362, vol. 54, Online.

* cited by examiner

CROSSLINK BREAKERS FOR PRESERVATION OF BIOLOGICAL SUBSTANCES

CROSS REFERENCE TO RELATED APPLICATIONS

The present application claims the benefit of U.S. Provisional Application Ser. No. 61/886,209, filed on Oct. 3, 2013, the subject matter of which is herein incorporated by reference in its entirety.

FIELD OF THE INVENTION

The present invention relates generally to compositions containing an AGE crosslink breaker and methods of using the same to prevent the formation of advanced glycation end products and preserve body fluids, proteins, cells and tissues.

BACKGROUND OF THE INVENTION

The ability to store and preserve red blood cells (RBCs) for later re-infusion into patients is a technological development that has helped advance modern surgical practices. This preservation is scientifically challenging and the steps to achieving longer storage duration and higher quality re-infused red blood cells have been incremental. As soon as RBCs are collected from a donor, they begin to die as they coagulate, starve, lose adenosine triphosphate (ATP), 2,3-Bisphosphoglycerate (2,3-DPG), membrane surface area and integrity, and hemoglobin (Hb).

Initially, storage compositions were designed to be acidic to prevent the caramelization of the glucose during heat sterilization performed in the final production step. In the 1950s, adenine was discovered to be useful a useful additive to replace the adenine lost by deamination. Thereafter, in the 1970s it became desirable to remove plasma from collected whole blood for platelets and to manufacture of plasma derivatives. However, this has led to a reduction in the percent recovery of the resulting "packed RBC."

To overcome this deficiency, compositions known in the art as additive solutions have been developed to restore volume, nutrients, and other useful RBC stabilizers. Additive solution compositions for the preservation of RBCs after their separation from whole blood are intended to be tailored specifically to the needs of RBCs, and the development of certain additive solutions has extended RBC storage to about 6 weeks. However, RBCs stored in these solutions undergo steady deterioration. It has been observed that during continued refrigerated storage, glucose is consumed at a decreasing rate, as the concentration of metabolic waste, i.e. lactic acid and hydrogen ions, increases. Such a decrease in the rate of glucose metabolism leads to depletion of adenosine triphosphate ATP, which directly correlates to the recovery of RBCs when the cells are returned to the circulation. Additive solutions such as Adsol® (AS-1), Nutricel® (AS-3), Optisol® (AS-5), and ErythroSol® have been designed to extend the storage of RBCs at 1-6° C.

Almost all of the whole blood collected now is made into components, and the RBC fraction is stored as packed RBCs. For blood drawn into the additive solution systems, RBCs are packed by centrifugation, plasma is removed so that RBCs make up 80% of the volume, and then 100 ml of an additive solution is sterilely added. The resulting suspensions have a RBC volume fraction of approximately 55%. RBCs stored in conventional FDA-approved additive solutions can be stored for only 6 weeks with an acceptable 24-hour in vivo recovery.

To increase the time of acceptable in vivo recovery of RBCs re-infused into patients after a storage period, attempts have been made to improve the additive solutions and/or storage processes. For example, U.S. Pat. No. 8,709,707 and U.S. Pat. Pub. No. 2005/0233302 both to Hess et al., the subject matter of each of which is herein incorporated by reference in its entirety, describes compositions and methods for the storage of RBCs.

Increased duration of RBC storage remains an important consideration during periods when demand is high but intermittent, such as during wartime, natural disasters and for geographical regions that require transfusable blood but only on an inconsistent and sporadic basis. In fact, given the current level of reported waste due to expiration of the safe storage period prior to realization of a demand in general, increasing the duration of time that RBCs may be safely stored is an ongoing concern.

Furthermore, although considered generally safe, blood transfusions have noteworthy risks associated with them, particularly when the blood has been stored for several weeks prior to transfusion. Although the current FDA regulations allow blood storage for up to 42 days in approved solutions at 4° C., transfusion of RBCs stored for over 21 days have led to negative clinical outcomes for blood recipients.

For example, human studies have shown that transfusion of older RBC units loads to increased risk of mortality and morbidity in critically ill patients with acute lung injury, decreased peripheral tissue oxygenation in pediatric and elderly patients, decreased cerebral oxygenation in patients with traumatic brain injury, and multiple organ failure as reported in Cho et al., *The road to advanced glycation end products: a mechanistic perspective*, Curr. Med. Chem. (2007) Vol. 14, pp. 1653-1671 and Vasan et al., *Therapeutic potential of breakers of advanced glycation end product-protein crosslinks*, Arch. Biochem. Biophys. (2003) Vol. 419, pp. 89-96.

The loss of RBC integrity during storage has been ascribed to a number of causes, including formation of advanced glycation end-products (AGEs)—a heterogeneous mixture of compounds formed by chemical reactions between specific sugars and proteins.

During the storage of collected RBC units, AGEs are thought to accumulate over time, due to the high amounts of glucose present in currently approved storage buffers. In fact, human RBCs stored in a FDA approved storage solution (adenine, dextrose, sodium chloride, and mannitol) showed a three-fold increase in the AGE levels compared to fresh blood.

AGEs are considered toxic to cells and may contribute to complications after RBC transfusion. Additionally, these accumulating AGEs may be responsible for increasing the immunogenicity of RBCs, resulting in decreased survival of RBCs.

Thus, there remains a need for improved RBC storage that results in longer storage duration, better recovery percentage, and improved physiological functioning of the transfused RBC. Consequently, there remains a need for improved RBC storage solutions and processes of manufacture thereof. There is also a continuing need for additive solutions which allow the RBC suspension to which the solution is added to be directly infused into humans, and which permit an acceptable post-infusion recoverability of viable RBCs possessing enhanced physiological functioning capabilities and lower rates of clearance from the infused patient's circulation.

The inventors of the present invention have found that AGE crosslink breakers can be used as a component of an additive solution that allows more effective recovery of RBCs during storage by retarding and reversing AGE formation on blood cells.

As described herein, AGEs are formed on RBCs during storage with glucose and lead to immunogenicity. The inventors of the present invention set out to determine a method to better preserve blood products by inhibiting this degradation pathway of RBCs.

SUMMARY OF THE INVENTION

It is an object of the present invention to provide a compound capable of preventing the formation of advanced glycation end products.

It is another object of the present invention to provide a compound for preserving body fluids, proteins, cells and tissues.

It is another object of the present invention to provide a compound for preserving blood and blood products.

It is another object of the present invention to provide a compound for preserving the quality of red blood cells.

It is another object of the present invention to improve the quality of red blood cells during long-term storage.

It is another object of the present invention to provide an improved means of stabilizing red blood cells.

It is still another object of the present invention to improve time of acceptable in vivo recovery of RBCs after storage.

It is still another object of the present invention to prevent hemolysis and maintain red blood cell integrity during long-term storage.

It is another object of the present invention to improve post-transfusion recovery of red blood cells.

To that end, in one embodiment, the present invention relates generally to a preservative for body fluids, proteins, cells and tissues comprising an effective amount of a compound of Structure (1):

(1)

wherein V, W, X, Y and Z are any atom suitable for a heterocyclic carbene or carbene precursor framework, including B, C, O, N, S, Se, P. and As in any chemically-feasible oxidation state;

wherein Q, R, M, T and U are any atom or substituent, including but not limited to, H, $CL_n$, $NL_n$, $PL_n$, $OL_n$, $SL_n$, $SeL_n$, $L_nCl$, $L_nBr$, $L_nI$, wherein L is any atom, substituent or group, and n is any integer such that Q, R, M, T, and U can access all chemically-feasible oxidation states; and wherein G comprises any charged counter ion including, but not limited to those derived from C, O, N, B, Al, S, Se, Cl, Br, I in any chemically-feasible oxidation state.

DETAILED DESCRIPTION OF THE PREFERRED EMBODIMENTS

Advanced glycation end-products (AGEs), a heterogeneous mixture of compounds formed by the non-enzymatic chemical reactions between sugars and the nucleophilic residues of proteins, have been detected on human red blood cells (RBCs). AGEs increase with storage duration and are believed to be responsible for or at least contribute to harmful (e.g., immunogenicity) effects, and the decreases in viability, of stored RBCs. When RBCs were stored with AGE crosslink breakers (such as PTB or ALT-711), the inventors of the present invention observed higher levels of intact RBCs and lower immunogenicity. Based thereon, it can be seen that AGE crosslink breakers can help preserve blood products by preventing AGE formation on RBCs and/or by breaking AGE crosslinks.

In one embodiment, the present invention relates generally to an AGE crosslink breaker having the Structure (1)

(1)

wherein V, W, X, Y and Z are any atom suitable for a heterocyclic carbene or carbene precursor framework, including B, C, O, N, S, Se, P, and As in any chemically-feasible oxidation state;

wherein Q, R, M, T and U are any atom or substituent, including but not limited to, H, $CL_n$, $NL_n$, $PL_n$, $OL_n$, $SL_n$, $SeL_n$, $L_nCl$, $L_nBr$, $L_nI$, wherein L is any atom, substituent or group, and n is any integer such that Q, R, M, T, and U can access all chemically-feasible oxidation states; and wherein G comprises any charged counter ion including, but not limited to those derived from C, O, N, B, Al, S, Se, Cl, Br, I in any chemically-feasible oxidation state.

Depending on the ligand, n can be any integer from 0 to 7, and in some embodiments, n may be an integer from 0-6.

One example of Structure (1) is a compound of Structure (2):

(2)

Examples of other compounds of Structure (1), include, but are not limited to, structures (3) to (10) below:

(3)

(4)

(5)

(6)

(7)

(8)

(9) and (10)

Of these compounds, Structures (5), (8) and (10) are particularly preferred.

PTB and ALT-711 are believed to cleave AGE crosslinks and scavenge α-dicarbonyls, a reactive species that give rise to AGEs. As described herein, the co-storing of RBCs with AGE crosslink breakers can reduce AGE formation and the consequent increase in immunogenicity.

These AGE crosslink breakers are simple to make and are non-toxic, as has been shown in animal studies and clinical trials with ALT-711.

In one embodiment, the present invention relates generally to the use of an effective amount of a crosslink breaker of Structure (1) described herein, having the ability to prevent the formation of Advanced Glycation End-products (AGEs) for the purpose of preserving body fluids, proteins, cells, and tissues, including but not limited to blood and blood-derived products. The use of a crosslink breaker of Structure (1) has been found to be suitable for stabilizing blood products such as RBCs.

Thus, in one embodiment, the present invention relates generally to a preservative for body fluids, proteins, cells and tissues comprising an effective amount of a compound of Structure (1):

(1)

wherein V, W, X, Y and Z are any atom suitable for a heterocyclic carbene or carbene precursor framework, including B, C, O, N, S, Se, P, and As in any chemically-feasible oxidation state;

wherein Q, R, M, T and U are any atom or substituent, including but not limited to, H, $CL_n$, $NL_n$, $PL_n$, $OL_n$, $SL_n$, $SeL_n$, $L_nCl$, $L_nBr$, $L_nI$, wherein L is any atom, substituent or group, and n is any integer such that Q, R, M, T, and U can access all chemically-feasible oxidation states; and wherein G comprises any charged counter ion including, but not limited to those derived from C, O, N, B, Al, S, Se, Cl, Br, I in any chemically-feasible oxidation state.

For ALT-711, the counter ion G is Cl—. It is noted that ALT-711 is also referred to herein as OCR6043.

As described herein the compounds of Structure (1) are capable of preventing formation of advanced glycation end products on RBCs. As also described herein, the preservative is suitable for stabilizing red blood cells and the use of the compounds of Structure (1) help preserve blood products through the prevention of AGE formation on RBCs.

The present invention also relates generally to the in vivo use of an effective amount of a crosslink breaker of Structure (1) described herein, having the ability to prevent the formation of advanced AGEs for the purpose of preserving body fluids, proteins, cells, and tissues, including but not limited to blood and blood-derived products. More particularly, the use of a crosslink breaker of Structure (1) has been found to be suitable for the in vivo stabilization of blood products such as RBCs.

The present invention also relates generally to the in vitro use of an effective amount of a crosslink breaker such as described herein, but not limited to the cross-link breakers described herein, having the ability to prevent the formation of AGEs for the purpose of preserving body fluids, proteins, cells, and tissues, including but not limited to blood and blood-derived products. More particularly, the use of an AGE crosslink breaker of Structure (1) has been found to be suitable for the in vitro stabilization of blood products such as RBCs.

The present invention also relates generally to the er vivo use of an effective amount of a crosslink breaker such as described herein, but not limited to the cross-link breakers described herein, having the ability to prevent the formation of AGEs for the purpose of preserving body fluids, proteins, cells, and tissues, including but not limited to blood and blood-derived products. More particularly, the use of an AGE crosslink breaker of Structure (1) has been found to be suitable for the ex vivo stabilization of blood products such as RBCs.

The present invention also relates generally to a method of preventing the formation of AGEs using a cross-link breaker such as the AGE crosslink breaker of Structure (1) in a minimum effective amount for the purpose of preserving body fluids, proteins, cells, and tissues, including but not limited to blood and blood-derived products.

The present invention also relates generally to a method of preventing the formation of AGEs using a cross-link breaker such as the AGE crosslink breaker of Structure (1) in a maximum effective amount for the purpose of preserving body fluids, proteins, cells, and tissues, including but not limited to blood and blood-derived products.

The present invention also describes various methods for the synthesis of AGE crosslink breakers having the general Structure (1) described above and including AGE crosslink breakers such as PTB and ALT-711.

The AGE crosslink breakers described in Structure (1) can be used in various methods for therapeutic intervention requiring the preservation of a proteins, cells, and tissues, including but not limited to, blood and blood-derived products, diagnostic methods requiring the preservation of a proteins, cells, and tissues, including but not limited to blood and blood-derived products, and methods of preserving proteins, cells, and tissues, including but not limited to blood and blood-derived products, for research purposes.

The inventors of the present invention have found that AGE crosslink breakers of Structure (1) are effective not only in inhibiting AGE formation, but also in reversing some of the already formed AGE products, making it a powerful AGE-combating compound.

ALT-711 (also referred to herein as OCR6043) has been found to exhibit significant effects on prolonging the shelf life of stored RBCs, presumably through the prevention of AGE precursor (α-dicarbonyl) formation.

Figure 1:
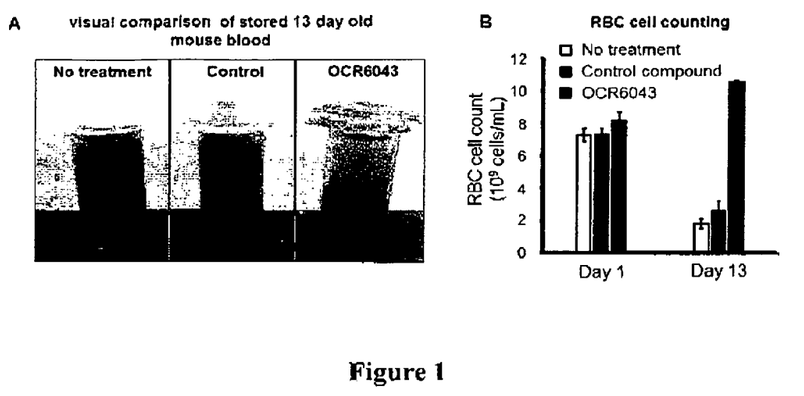
FIG. 1 depicts addition of OCR6043 improved mouse RBC viability under typical storage conditions.

Specifically, the addition of OCR6043 improved mouse RBC viability under typical storage conditions as can be seen in FIG. 1 and as described in Example 2 below.

FIG. 1 illustrates OCR6043-mediated prolonging of the integrity of stored RBCs. Leuko reduced mouse blood was stored under FDA-approved storage conditions (CPDA-1 buffer at 4° C.) for up to 13 days, in either OCR6043, control compound (structurally similar to OCR6043, but nonfunctional as a AGE crosslink breaker), or without any additive. FIG. 1 illustrates that under these conditions, the untreated and control-treated stored blood showed hemolysis (cloudy red supernatant), whereas OCR6043-treated samples were unhemolyzed (clear supernatant). FIG. 1 also illustrates that hemocytometer-based analysis of RBCs revealed superior cell viability in OCR6043-treated conditions.

AGE crosslink breakers such as ALT-711 are easy to synthesize and non-toxic to animals and humans (as has been shown in various animal studies and a number of clinical trials). ALT-711 has been tested as a potential treatment for cardiovascular disease as described in U.S. Pat. Pub. No. 2009/0124674 to Egan et al., the subject matter of which is herein incorporated by reference in its entirety, and for the treatment of disorders associated with protein aging as described in U.S. Pat. Pub. No. 2002/0022622 to Wagle et al., the subject matter of which is herein incorporated by reference in its entirely.

Advanced glycation end-products are heterogeneous mixtures of compounds formed by the non-enzymatic chemical reactions between sugars and the nucleophilic residues of proteins, and have been implicated in the pathogenesis of a number of diseases. ALT-711 is a therapeutic agent developed for cardiovascular diseases that was proposed to cleave pro-formed AGE-protein crosslinks. Despite promising results in animal models and clinical trials, its mechanism of action still remains controversial.

We report the systematic investigations into the dicarbonyl cleavage by ALT-711. We demonstrate that it is capable of cleaving α-diketones more efficiently and likely via a distinct mechanism, compared with other N-heterocyclic carbene precursors. We also found that ALT-711 reacts rapidly with α-keto aldehydes to form the corresponding cycloadducts. This work suggests ALT-711 may be especially suited for α-dicarbonyl clearance. To this end, these findings provide insights into the optimization of next-generation crosslink breakers.

Figure 3A:
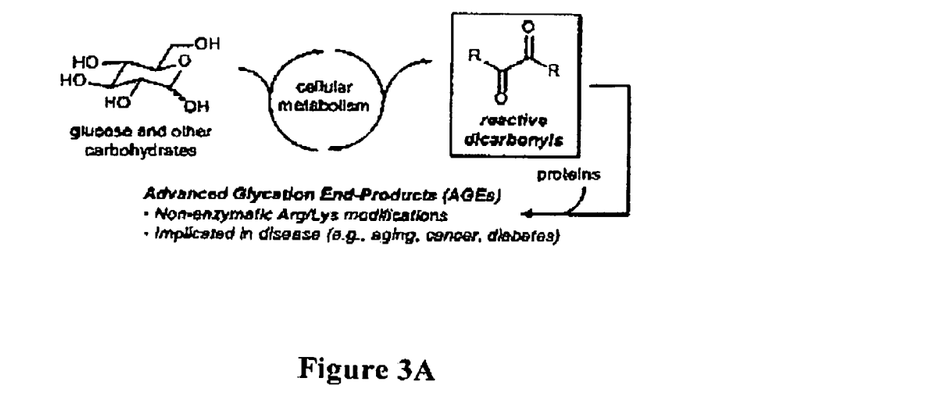
FIG. 3A depicts reactive dicarbonyl intermediates that are formed as byproducts of carbohydrate metabolism, and lead to the formation of AGEs, a class of non-enzymatic post-translational modifications of protein Arg and Lys side-chains that are implicated in various diseases.
Figure 3B:
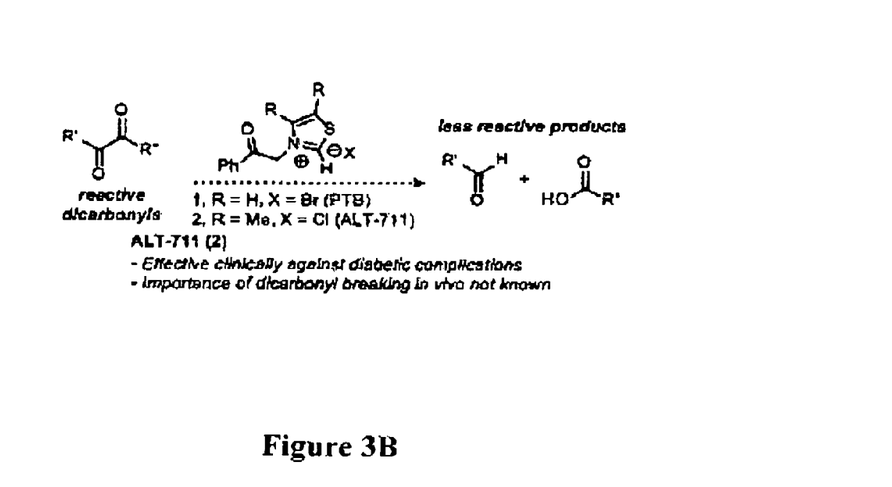
FIG. 3B depicts phenacylthiazolium salts proposed to cleave dicarbonyls under aqueous conditions to afford less reactive products.

The non-enzymatic post-translational modifications of proteins, termed "protein glycation." occurs in all living organisms due to spontaneous reactions between amino/guanidino groups in proteins and carbonyl groups found in carbohydrates and their metabolites. The products of protein glycation, termed advanced glycation end-products (AGEs), have been implicated in various pathological processes (e.g., diabetes, cancer, Alzheimer's disease and normal aging), arising from their ability to rigidify proteins by crosslinking and also to interact with various cell-surface receptors. Because protein glycation is not enzymatically regulated, levels of AGE formation depend on several factors including the concentrations, reactivity profiles, and duration of exposure of reactive carbonyl metabolites.

α-Dicarbonyls are among the most reactive AGE precursors found in vivo, and therefore, agents capable of decreasing their levels have been sought for therapeutic purposes. To this end, Cerami et al., *An agent cleaving glucose-derived protein crosslinks in vitro and in vivo*, Nature (1996) vol. 382, pp. 275-278, proposed that N-phenacylthiazolium bromide (PTB) might be effective in preventing AGE-mediated tissue damage by catalyzing the conversion of α-dicarbonyls into relatively less reactive aldehyde and carboxylic acid byproducts as depicted in FIG. 1B. Cerami demonstrated that PTB could indeed transform α-diketone 3 (1-phenyl-1, 2-propanedioic, PPD) into benzoic acid (PhCO2H) and also prevent AGE-formation and protein aggregation in vitro. U.S. Pat. No. 5,853,703 to Cerami, the subject matter of which is herein incorporated by reference in its entirety, describes compositions and method for inhibiting and reversing nonenzymatic cross-linking (protein aging) and describes compositions comprising an agent capable of inhibiting the formation of advanced glycosylation end products by cleaving α-dicarbonyl-based protein crosslinks present in the advanced glycosylation end products. Subsequently, a more stable variant of PTB was developed, and this agent (ALT-711) was found to exhibit beneficial effects in various animal models of diabetes and aging. ALT-711 was advanced to human clinical trials for age-related arterial-stiffening by Alteon Pharmaceuticals. Despite leading to improvements against certain clinical endpoints, development of ALT-711 was halted alter completion of Phase 2 studies.

The unusual mode of action proposed for ALT-711 has led to significant controversy in the academic literature. Although several independent research groups have confirmed that PTB and ALT-711 can convert PPD into benzoic acid, many studies have argued against the involvement of dicarbonyl cleavage in clinical findings. For example, Yang et al., *AGE-breakers cleave model compounds, but do not break Maillard crosslinks in skin and tail collagen from diabetic rats*, Arch Biochem Biophys (2003) Vol. 412, pp. 42-46, was unable to obtain evidence that PTB or ALT-711 could break AGE crosslinks in vitro and based on further studies (Price et al., *Chelating activity of advanced glycation end-product inhibitors*, J Biol Chem (2001), Vol. 276, pp. 48967-48972), suggested that in vivo effects result from potent antioxidant and/or metal-chelating activity. Thornalley et al., *Rapid hydrolysis and slow alpha,beta-dicarbonyl cleavage of on agent proposed to cleave glucose-derived protein cross-links*, Biochem Pharmacol (1999), Vol. 57, pp. 303-307, has shown that PTB decomposes rapidly under physiological conditions with a 44 minute half-life, and that the dicarbonyl cleavage reaction could only compete with decomposition pathway at non-physiologically high concentrations. Furthermore, Biemel et al., *Site-specific quantitative evaluation of the protein glycation product N-6-(2,3-dihydroxy-5,6-dioxohexyl)-L-lysinate by LC-(ESI)MS peptide mapping: Evidence for its key role in AGE formation*, Bioconjug Chem (2003) Vol. 14, pp. 619-628 reported that AGE-derived crosslinks likely form by way of protein-bound α-keto aldehyde intermediates, and probably do not contain α-diketone substructures.

Recently, structurally similar compounds C16 (Grandhee et al., *Mechanism of Formation of the Maillard Protein Cross-Link Pentosidine—Glucose, Fructose, and Ascorbate as Pentosidine Precursors*, J Biol Chem (1991) Vol. 266, pp. 11649-11653). C36 (Chow et al., *Catalytic Generation of Activated Carboxylates: Direct, Stereoselective Synthesis of β-Hydroxyesters from Epoxyaldehydes*, J Am Chem Soc (2004) Vol. 126, pp. 8126-8127), TRC4149 (Fischer et al., *Umpolung of Michael acceptors catalyzed by N-heterocyclic carbenes*. J Am Chem Soc (2006), Vol. 128, pp. 1472-1473), and TRC4186 (Tsuge O, *Stereochemical study on 1,3-dipolar cycloaddition reactions of heteroaromatic N-ylides with symmetrically substituted cis and trans olefins*, Bull Chem Soc Jpn (I 985) Vol. 58, p. 3137) were reported to exhibit crosslink breaking activities such as releasing BSA from AGE-BSA-collagen complexes, increasing tail-tendon solubility, and improving cardiovascular function in diabetic rats. However, their mechanisms of action have yet to be studied.

Surprisingly, no investigations into aqueous-phase α-dicarbonyl cleavage processes have yet appeared in the scientific literature (apart from simple reactions between 1 or 2 with PPD). Here we take the first step in evaluating the viability of this novel and potentially transformative mode of therapeutic action. The studies reported herein have led to several notable findings. For example, we have found that phenacylthiazolium carbenes cleave α-diketones under aqueous conditions and do so more efficiently, and through a distinct mechanism, as compared to N-benzyl-derived N-heterocyclic carbenes (NHCs). Furthermore, ALT-711 rapidly reacts with α-keto aldehydes to form cycloadducts, which are not observed in reactions with other NHC precursors. Finally, we propose plausible mechanistic models to explain the increased reactivity of N-phenacyl-derived thiazolium salts, along with their propensity for cycloaddition.

The studies reported herein represent the first "head-to-head" comparison between different NHC precursors for their activity in cleaving the dicarbonyl C—C bond, along with the first direct evidence that N-phenacyl thiazolium salts may be uniquely suited to react with α-dicarbonyls under aqueous conditions. Furthermore, because the major dicarbonyl-based AGE precursors in vivo are believed to be of the α-keto aldehyde structural class, these studies provide a unifying explanation for how ALT-711 might function therapeutically, while also illuminating pathways for the optimization of next-generation analogues. To the extent that it provides support for Cerami's original model, in which ALT-711 functions in vivo as a selective mediator of C—C bond fragmentation, this work has the potential to reinvigorate a novel and under-explored mode of action for small-molecule therapeutics.

EXAMPLES

Example 1

Materials and Methods

Chemicals

Chemicals were purchased from Aldrich or Alfa Aesar and used as received unless noted otherwise. PTB, 3-benzyl-4,5-dimethylthiazol-3-ium chloride and 1,6-diphenyl-hexane-3,4-dione were prepared as described in the literature. Synthetic procedures and characterization data for compounds are described in Supplementary Material.

Dicarbonyl cleavage reactions were performed using either the method described in Vasan et al., *An agent cleaving glucose-derived protein crosslinks in vitro and in vivo*, Nature (1996) Vol. 382, pp. 275-278 (Method A) or a modified method with MeCN as a co-solvent (Method B).

Method A

PPD (21 μl, 156 μmol) was added to a murky solution of NHC (2 or 4, 71 μmol) in 50% MeOH/0.5 M pH 7.4 sodium phosphate buffer (3.5 ml/3.5 ml; final conc. 10 mM NHC, 22 mM PPD) and kept stirred at 37° C. Approximately 0.5 ml aliquots were taken at stated times and analyzed by HPLC. Experiments using EtOH or iPrOH as a co-solvent were done in the same manner. Concentrations of benzoic acid and benzoate esters were determined by peak integration against the calibration curves.

Method B 60 mM solution of dicarbonyl substrate (45 μmol) in MeCN (0.75 ml) was added to 20 mM solution of NHC (15 μmol) in 0.15 M pH 7.4 sodium phosphate buffer (0.75 ml) and kept stirred at 37° C. At stated times, 75 μl aliquots were taken, diluted with 50% MeCN/H2O (425 μl) and analyzed by LCMS with 2,4-dihydroxyquinoline (248 μM) as an internal standard. The cleavage products were quantified by peak integration against the calibration curves.

ALT-PGO (19)

Phenylglyoxal hydrate (16; 114 mg, 0.75 mmol, 2 eq) was added to a solution of ALT-711 (2; 100 mg, 0.37 mmol) in 50% MeCN/0.15 M pH 7.4 phosphate buffer (total vol. 37 ml) and kept stirred at room temperature for 15 mins. The reaction mixture was cooled to −20° C. to precipitate out sodium phosphate as white crystals. The supernatant was transferred, and the residue was washed with MeCN and combined with the supernatant. This yellow clear solution was concentrated at room temperature to remove MeCN and purified by HPLC (16-27MeCN over 31 min). Fractions were collected and lyophilized to give three diastereomers (ALT-PGO-1 through ALT-PGO-3) as white solids (55% combined yield). See Supplementary Material for characterization data.

ALT-MGO (20)

Four diastereomers (ALT-MGO-1 through ALT-MGO-4) were obtained with a similar method to ALT-PG using 2 (100 mg, 0.37 mmol) and 40% methylglyoxal (MOO, 17) solution (0.2 ml, 1.3 mmol, 3.5 eq). Purification was performed by HPLC (9-19% MeCN over 32 min), and the lyophilization of fractions afforded the title compounds as white solids (96% combined yield). See Supplementary Material for characterization data.

For trapping under physiological conditions (FIG. 5), 12.5 µl of 2 (40 mM stock) and 7.7 µl of MGO (6.5 mM stock) were added to PBS (4.98 ml) and kept stirred at 37° C. At stated times, 445 µl of the reaction mixture was taken, quenched with 1 M HCl (5 µl) and analyzed by LCMS after adding 50 µl of 3 mM 4-methoxybenzhydrol as an internal standard. Yield of ALT-MGO (20) was determined by peak integration (m/z=304) against a calibration curve.

Results and Discussion

Although applications of thiazolium salts and other NHC precursors for organic synthesis have been widely explored during the past 10 years, only a few studies have focused on N-phenacyl-derived NHCs. For example, in addition to their ability to cleave PPD under aqueous conditions. N-phenacyl-derived thiazolium salts have been shown to participate in 1,3-dipolar cycloaddition reactions with alkenes/alkynes, and to undergo nucleophilic addition reactions with isocyanates and isothiocyanates. Reactions between NHCs and α-dicarbonyls have also been under-explored, and have primarily focused on using α-diketones as acyl anion equivalents in benzoin-type condensations and Stetter reactions in organic solvent systems.

Thus, our first goal in these studies was to assess the ability of various NHC precursors to induce the degradation of the dicarbonyl model substrate (PPD, 3). To this end, we screened the thiazolium (4-6), benzothiazolium (7), triazolium (8,9) and imidazolium (10) halide substructures shown in Table 1. These experiments revealed that only a relatively small subset of NHC precursors could induce $PhCO_2H$ formation from 3. N-phenacyl derivative ALT-711 (2) gave rise to the highest overall yield of dicarbonyl cleavage products, while somewhat surprisingly, N-benzyl thiazolium salt 4 and thiamine derivatives 5, 6 led to substantially lower yields suggesting the importance of the phenacyl group.

Both benzothiazolium (7) and triazolium (8) salts, which have respectively been shown to exhibit faster H/D exchange kinetics at C(2) and higher reactivities in condensation and p-alkylation reactions compared to thiazolium derivatives, also afforded no observable levels of benzoic acid. Instead, 7 gave rise predominantly to an oxalamide derivative, which is believed to form via dimerization and oxidation of intermediate carbenes. Replacing the N-benzyl substituent in 8 with a phenacyl group (9) restores the reactivity to a small extent whereas substitution of the triazole core in 9 with an imidazolium nucleus (10) did not produce any benzoic acid. Stability studies afforded additional insights. Whereas N-benzyl-derived species 4-6 were found to be quite stable under the reaction conditions, compound 2 was observed to disappear from solution upon exposure to PPD.

TABLE 1

Cleavage of 3 to benzoic acid by N-heterocyclic carbenes.

| NHC | Yield (%)[a] |
|---|---|
| 2 | 60 |
| 4 | 20 |
| 5 | 14 |
| 6 | 9 |
| 7 | 0[b] |
| 8 | 0[b] |

TABLE 1-continued

Cleavage of 3 to benzoic acid by N-heterocyclic carbenes.

Ph—C(O)—C(O)—Me (3) + NHC (0.33 eq) → [phosphate buffer (pH 7.4), 50% MeCN, 37° C., 12 h] → Ph—C(O)—OH

| NHC | Yield (%)[a] |
|---|---|
| 9 (N-methyl-triazolium with N-phenacyl, Cl⁻) | 12 |
| 10 (N-methyl-imidazolium with N-phenacyl, Cl⁻) | 0[b] |

[a]Yields were determined by peak integration in LCMS with respect to 3.
[b]Benzoic acid formation not detectable above background (5%).
Cleavage experiments were performed according to Method B.
Ar = (4-amino-2-methylpyrimidin-5-yl).

Taken together, these results suggest several notable conclusions. For example, efficient α-dicarbonyl cleavage requires both a thiazolium scaffold and N-phenacyl substituent on the NHC precursor and does not depend solely on the pKa of the heterocycle core. Also, based on the striking differences in yield of benzoic acid and fate of the NHC over the course of the reaction, we propose that thiazolium-derived NHC precursors produce benzoic acid through discrete mechanisms: N-benzyl derivatives (4-6) react slowly with the dicarbonyl substrate but are capable of catalytic turnover, while the N-phenacyl-substituted compound may operate via both a catalytic and a stoichiometric mechanism that results in the consumption of the catalyst.

Having learned that ALT-711 performed best among NHCs evaluated for PPD cleavage, we sought to test its substrate scope versus its N-benzyl counterpart (4). We therefore measured product distribution and yield while varying the co-solvent used to solubilize dicarbonyl substrates. As summarized in Table 2, we first investigated the performance of alcoholic co-solvents in PPD cleavage reactions. Replacing MeCN co-solvent with MeOH led to the production of both methyl benzoate (PhCO₂M) and benzoic acid in comparable combined yields, irrespective of NHC precursor employed (Entries 2 and 4). Despite this, however, the product distributions differed substantially: ALT-711 (2) predominantly afforded benzoic acid (PhCO₂H: PhCO₂Me=3.2:1, Entry 2), whereas 4 mostly gave rise to methyl benzoate (PhCO₂H:PhCO₂Me=1:2.2, Entry 4). Further replacement of the co-solvent with EtOH and i-PrOH in 4-catalyzed reactions led to a decrease in the proportion of ester production, still without altering overall yield (Entries 5 and 6). Notably, replacing ALT-711 with PTB led to a slight decrease in overall product yield, likely due to the instability of this heterocycle, but a 3:1 PhCO₂H:PhCO₂Me ratio was preserved.

TABLE 2

Efforts of solvent and NHC precursor on reaction outcome

| Entry | NHC precursor | Co-solvent | Product(s) | Product ratio | Combined % Yield[a] |
|---|---|---|---|---|---|
| 1[b] | 2 | MeCN | PhCO₂H | NA | 61 |
| 2[c] | 2 | MeOH | PhCO₂H, PhCO₂Me | 3.2:1 | 54 |
| 3[b] | 4 | MeCN | PhCO₂H | NA | 20 |
| 4[c] | 4 | MeOH | PhCO₂H, PhCO₂Me | 1:2.2 | 62 |
| 5[c] | 4 | EtOH | PhCO₂H, PhCO₂Et | 1.3:1 | 60 |
| 6[c] | 4 | i-PrOH | PhCO₂H, PhCO₂iPr | 1.0:0 | 58 |
| 7[c] | 1 | MeOH | PhCO₂H, PhCO₂Me | 3.0:1 | 39 |

[a]Yields were determined by peak allegration in LCMS with respect to dicarbonyls.
Experiments were performed according to [b]Method B or [c]Method A.
PhCO₂Et = ethyl benzoate: PhCO₂iPr = isopropyl benzoate.

These results provide further evidence that N-phenacyl- and N-benzyl-derived NHC precursors cleave dicarbonyls through distinct mechanisms. The disparate trends in acid:ester ratio might suggest that product determination proceeds rapidly through pathways that depend on N-substitution patterns, while the comparable overall yields in alcoholic solvents, which mirror the observed rates of product formation in these reactions, likely reflect similarities in the rate-determining step (e.g., carbonyl addition).

Figure 4:
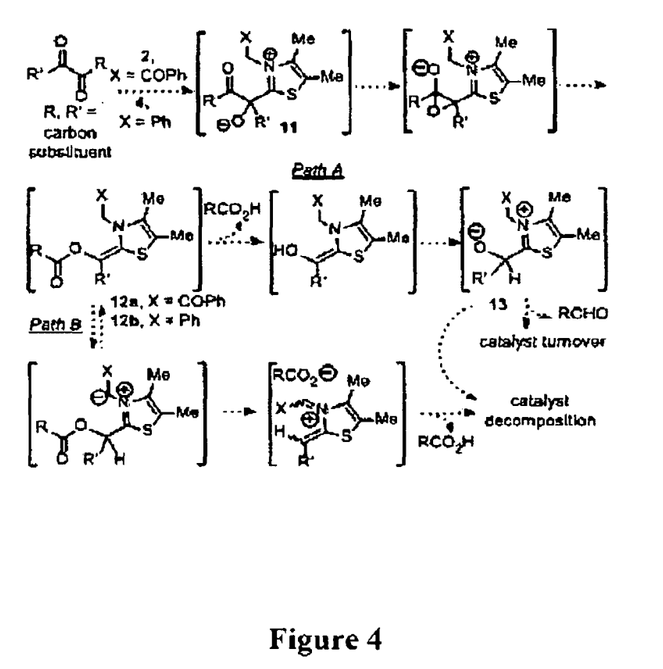
FIG. 4 depicts a proposed mechanism for α-diketone cleavage by ALT-711 (2) and its benzyl counterpart (4). ALT-711 can mediate the cleavage by ester solvolysis (path A) and/or phenacyl-assisted acid expulsion (path B) whereas 4 can only catalyze the reaction via path A.

A mechanistic proposal that is consistent with these and prior observations is depicted in FIG. 4. Thus, rate-determining carbonyl addition, followed by rearrangement of 11 to form intermediate enol esters 12, could proceed either through enol-ester solvolysis (path A) or phenacyl-assisted acid expulsion (path B). One would expect that the rate of flux through path A would reflect the relative rates of hydrolysis versus alcoholysis of 12, while that of path B would be independent of solvent nucleophilicity, and rely only on the enolate-mediated expulsion of acid. Observed product distributions, then, would arise because 12a can form products through paths A or B, whereas 12b can only proceed through path A.

In cleavage of PPD with ALT-711 (2), we detected several decomposition products of the catalyst that appear to be adducts between 2 and an acetyl group, the remainder of PPD following the release of benzoic acid. One adduct that has been isolated and characterized explains why the concentration of ALT-711 diminishes after cleaving PPD while the benzyl counterpart (4) behaves as a stable catalyst. Instead of liberating acetaldehyde and re-entering the catalytic cycle, oxidation of alcohol 13 to the corresponding methyl ketone followed by an aldol condensation with the phenyl ketone gives rise to a thiazolopyridinium derivative (see Supplementary Material for details). N-benzyl species (4-6) do not have this mechanism for the destruction of the catalyst, and they are therefore stable over the course of the cleavage reaction.

The superior reactivity of ALT-711 to that of 4-6 may be attributable to the electron-withdrawing effect of the phenacyl group, leading to a decrease in the C(2) pKa and/or a corresponding increase in the rate of equilibration between thiazolium and more reactive tautomers. Benzothiazolium and perhaps triazolium carbenes, on the other hand, may not be sufficiently nucleophilic at C(2) to react with dicarbonyls and, therefore, preferentially undergo dimerization, while the less acidic imidazolium salt 10 does not give rise to appreciable concentrations of reactive carbene or dipole species. More detailed investigations into the mechanism(s) of this process are currently ongoing.

Our efforts to investigate the scope of thiazolium salt-mediated reactions with dicarbonyls began with bis-alkyl diketone 14 (Table 3, Entry 1). This substrate is cleaved cleanly by 2, and affords acid 18 in 82% yield. NHC precursor 4, on the other hand, provides 18 in only 14% yield (Entry 2). The efficiency of dicarbonyl cleavage reactions decreases substantially in the case of benzil (15, Entry 3), which affords benzoic acid in 14% and 1% yield following exposure to 2 and 4, respectively.

TABLE 3

Scope of NHC-mediated reactions with alpha-dicarbonyls.

| Entry | Substrate | NHC precursor | Product | % Yield[a] |
|---|---|---|---|---|
| 1 | 14 | 2 | 18 | 82 |
| 2 | 14 | 4 | 18 | 14 |
| 3 | 15 | 2 | PhCO$_2$H | 14 |
| 4 | 15 | 4 | PhCO$_2$H | 1 |
| 5 | 16 | 2 | 19 | 55[b] |
| 6 | 16 | 4 | PhCO$_2$H | 30[c] |
| 7 | 17 | 2 | 20 | 96[b] |

[a]Yields were determined by peak integration in LCMS with respect to dicarbonyls unless noted otherwise.
[b]Isolated yield with respect to 2.
[c]Phenylglyoxal alone undergoes decomposition to give a substantial amount of benzoic acid (25%) under the reaction conditions.
Method B was used for all entries.

19 (R = Ph)
20 (R = Me)

Reactions involving α-keto aldehyde derivatives 16 and 17 followed an unexpected course. Treatment of these substrates with 2 led to instantaneous, high-yield production of a diastereomeric mixture of cycloadducts (19 and 20) that decompose to complex mixtures under the reaction conditions with half-lives of approximately 3 h Structures were determined based on in-depth NMR analysis (see Supplementary Material). The N-benzyl-derived NHC precursor (4) did not lead to rapid consumption of dicarbonyl starting material (16) and only afforded benzoic acid in low yields under the same conditions.

Figure 5:
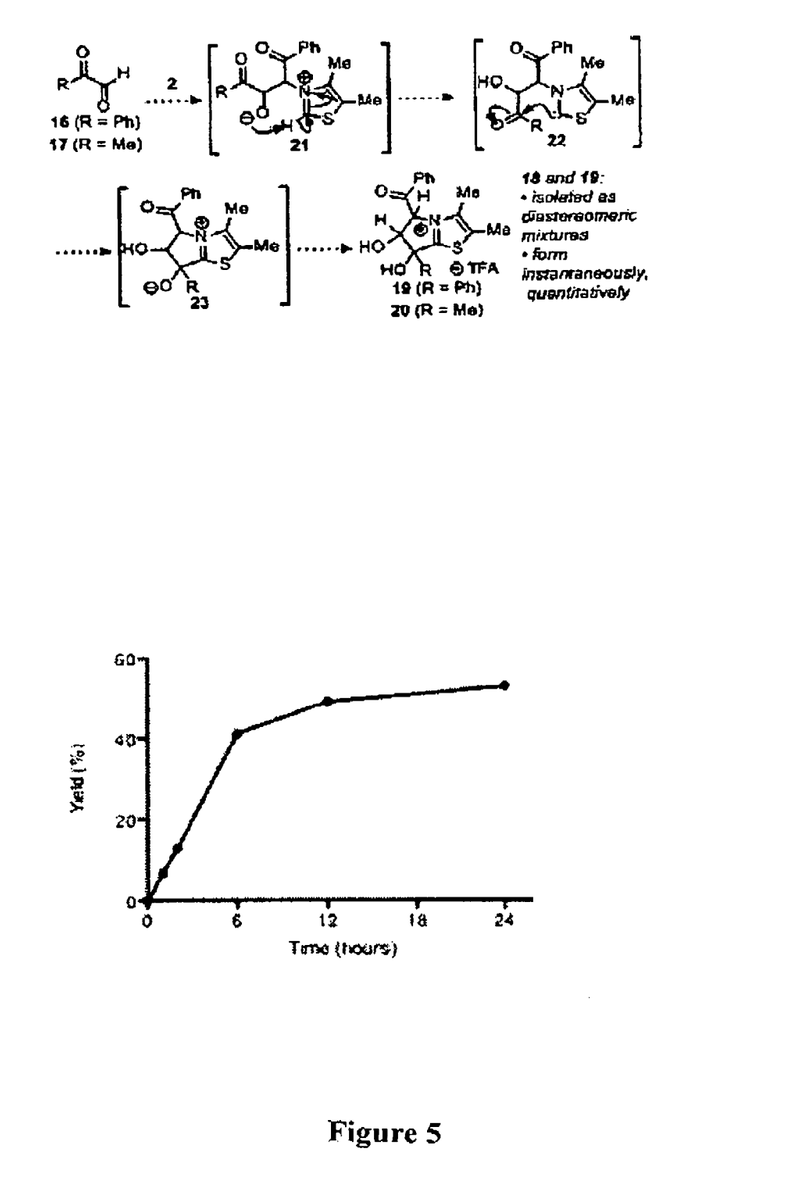
FIG. 5 depicts a proposed mechanism for the trapping of α-keto aldehydes by ALT-711 (2) and depicts ALT-711 traps MGO (17) to form cycloadducts (20) with a moderate yield under physiological conditions.

A plausible mechanism for the formation of 19 and 20 is shown in FIG. 5. Based on the regiochemistry of product formation, we hypothesize that C—C bond formation initially takes place between the N-phenacyl substituent and the sterically less hindered aldehyde carbonyl to provide 21. The high reactivity of the phenacyl α-carbon may arise either from its greater acidity versus the thiazolium C(2) position or an increased population of a zwitterionic tautomer of 2 under these reaction conditions. This observation is consistent with results from related systems wherein 4-methyl-3-phenacylthiazolium bromide reacts with isocyanate/isothiocyanate compounds to afford a-carbon alkylation products. Intramolecular proton transfer then provides carbene 22, and 5-exo-trig cyclization then affords a zwitterionic intermediate (23), which is readily protonated upon HPLC purification to deliver either 19 or 20 as the corresponding trifluoroacetate (TFA) salts.

Recognizing the reaction conditions employed above were non-physiological, we wanted to test if ALT-711 could efficiently trap methylglyoxal (MGO, 17) at a pathologically relevant concentration (4-6 μM). We obtained ALT-MOO adduct (20) in PBS with a 53% yield at 24 hours (FIG. 5B). This result is consistent with a study in which ALT-711 lowered MOO levels and attenuated MOO-induced glucose intolerance in rats. The trapping of MGO by ALT-711 may be the mechanism for the observed effects.

Interestingly, cycloadducts 19 and 20 are directly analogous to the products initially proposed by Cerami for reactions between 1 and putative diketone crosslinks. Our work provides support that such structures are indeed capable of forming under physiological conditions, albeit from reactions with α-keto aldehydes instead of α-diketones. The cleavage of α-diketones by ALT-711 may have limited physiological relevance because the reaction kinetics on the order of hours even at non-physiologically high concentrations are unlikely able to compete with the decomposition of the dicarbonyl species in vivo.

Here we provide the first systematic investigations into the dicarbonyl-cleaving activities of NHCs. Our data suggest that phenacyl-substituted NHC precursors react with α-dicarbonyl substrates more rapidly—and through distinct mechanistic pathways—compared to their N-benzyl-substituted counterparts. In aqueous-alcoholic solvent mixtures, for example, reactions with α-diketones are hypothesized to involve similar rate-determining steps (e.g., nucleophilic attack on dicarbonyl substrates) and distinct product-determining steps, as outlined above. Reactions of N-phenacyl thiazolium salts with α-keto aldehydes, on the other hand, proceed quite rapidly to provide formal cycloadducts, while those with the N-benzyl substituted analogs yield complex product mixtures. Taken together with evidence that α-keto aldehydes are critical intermediates in vivo for protein-protein crosslink formation, our data support a mechanism in which cycloaddition pathways may account for therapeutic actions of 2 in vivo.

To the extent that such stepwise cyclization reactions are operative in vivo, ALT's therapeutic efficacy might be enhanced through optimization of N-atom substituents, further exploration of NHC precursors, and suppression of known decomposition pathways.

Example 2

700 μL of Leukoreduced HOD blood—blood obtained from a transgenic mouse line expressing HEL-OVA-Duffy (HOD), which serves as a tag to track RBCs—was treated with either 2 mg of OCR6043, or control compound 1-methyl-4-phenacyl-triazolium chloride (MPTC; a compound that is structurally similar to ALT-711, but functionally inactive) to achieve a final concentration of 12 mM. This solution was stored at 4° C. according to FDA-approved conditions for 13 days. The 13 day time point was chosen because mouse blood deteriorates significantly faster than human blood. The steps to collect HOD blood from mice and the addition of the FDA-approved storage buffer CPDA are described in Hendrickson et al., *Transfusion of fresh murine red blood cells reverses adverse effects of older stored red blood cells*, Transfusion (2011) Vol. 12, pp. 2695-2702.

After the 13-day incubation of blood, it was revealed that OCR6043 was capable of preventing redness (a result of heme accumulation following RBC lysis) in blood sample supernatants compared to control conditions as depicted in FIG. 1. We also counted the intact RBCs using a hemocytometer after 13 days of storage as also depicted in FIG. 1. This data indicated that OCR6043 was able to prevent the lysis of RBC's seen in control treatments.

Figure 2A:
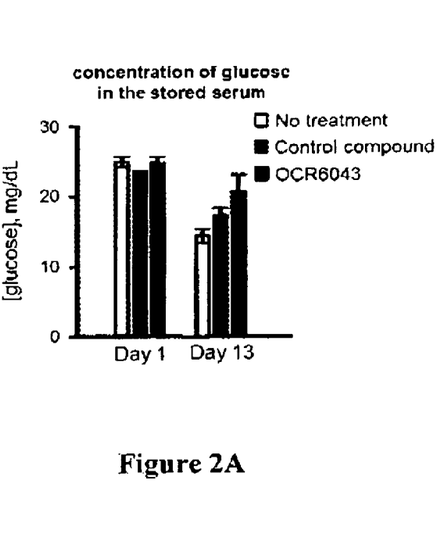
FIGS. 2A, 2B, 2C and 2D depict OCR6043-mediated preservation of glucose levels, inhibition of AGE precursor (α-dicarbonyl) formation, decreased immunogenicity, and more effective post transfusion recovery, of stored mouse blood.
Figure 2B:
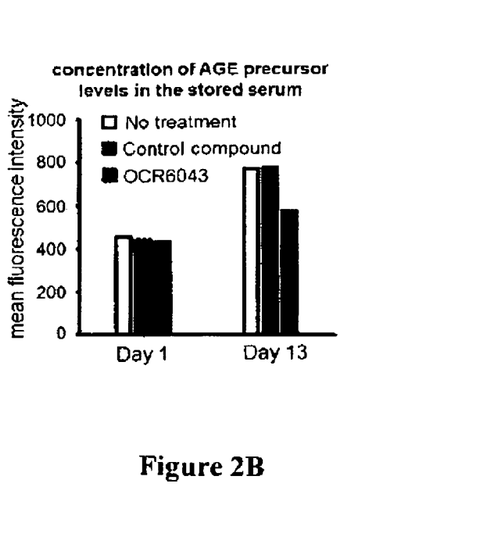
Figure 2C:
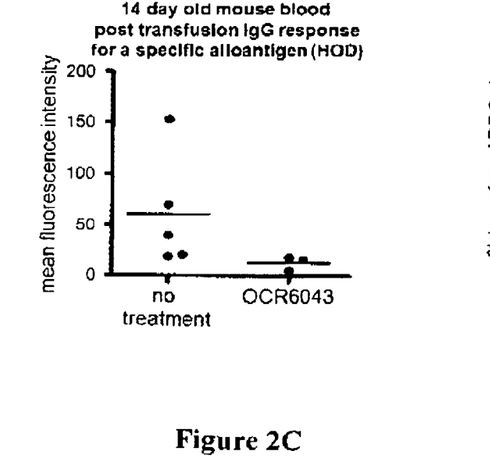
Figure 2D:
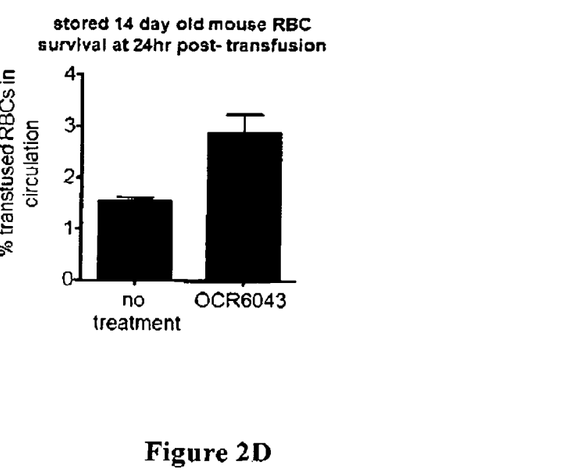

As illustrated in FIGS. 2A, 2B, 2C, and 2D, OCR6043-mediated preservation of glucose levels, inhibition of AGE precursor (α-dicarbonyl) formation, decreased immunogenicity, and more effective prost transfusion recovery, of stored mouse blood. Leuko-reduced mouse blood was stored under typical storage conditions for up to 14 days, in either OCR6043, control compound, or without any treatment. FIG. 2A illustrates an analysis of glucose in the serum from the stored blood was evaluated using a glucose oxidase enzymatic assay. The data indicated more effective preservation of glucose levels when incubated with OCR6043; note that majority of the glucose measured in this assay, originates from the storage buffer (CPDA-1). FIG. 2B illustrates the AGE precursor levels on RBCs were measured using a dicarbonyl-specific fluorophore that was developed in-house. The time dependent increase in the AGE precursor levels was dampened in the presence of OCR6043. FIG. 2C illustrates mouse blood that was stored for 14 days, was evaluated for its immunogenicity upon transfusion, by testing for IgGs against an alloantigen on the RBCs (HOD=HEL-OVA-Duffy). The results indicated decreased immunogenicity in OCR6043-treated samples. FIG. 2D illustrates that the indicated decreased immunogenicity in OCR6043-treated samples. FIG. 2D illustrates that the transfusion of stored blood treated with OCR6043, had a two-fold increase in cell survival in comparison to untreated stored blood 24 hours after transfusion.

OCR6043 treatment decreases immunogenicity, and enhances post-transfusion recovery of stored mouse blood. Leukoreduced mouse blood was stored under typical storage conditions for up to 14 days in either OCR6043 or without any treatment. This mouse blood was evaluated for its immunogenicity upon transfusion by testing for IgGs against an alloantigen on the RBCs (HOD=HEL-OVA-Duffy). The results indicated decreased immunogenicity in OCR6043-treated samples. The transfusion of stored blood treated with OCR6043 had a two-fold increase in cell survival in comparison to untreated stored blood 24 hours after transfusion.

Blood that was stored for 14 days with OCR6043 elicited decreased immune reactivity compared to the untreated older blood, when transfused and in circulation for 14 days.

As described herein, the stored blood has an HOD marker allowing facile detection after transfusion. We transfused 75 pL of stored blood into B6 mice (not expressing the HOD antigen). The IgG response against the ROD alloantigen on stored RBCs revealed increased IgG responses in mice 14 days following transfusion (FIG. 2A, no treatment). However, storing the blood with OCR6043 attenuated this immune response. The anti-HOD IgG response was evaluated using standard ELISA techniques described in Hendrickson et at. Similarly, transfusion of fresh HOD blood does not elicit a significant immune response (data not shown), indicating the immune response seen following transfusion of stored blood treated with OCR6043 is akin to transfusion of fresh blood.

Finally, mice transfused with aged blood (14 days old) stored with OCR6043 showed a twofold increase in circulating RBC survival at 24 hours following transfusion, compared to control conditions (FIG. 2B).

Using the transfusion methodology described in Hendrickson et al., it was possible to identify the surviving circulating RBCs using flow cytometry. An impressive two-fold increase in 24 hour post transfusion recovery of stored RBCs was seen in OCR6043-treated samples, in comparison to the untreated control.

Based thereon, it can be seen that these results indicate that OCR6043 represents an effective additive for blood preservative solutions to mitigate possible negative effects of transfusing blood that was stored for extended periods.

As can be seen, the compounds of Structure (1) can be used as an additive for blood preservative for whole blood or RBCs or other body solutions in an amount up to the solubility of the particular compound.

The use of the these compounds in an effective amount for preservation of RBCs prevents the formation of advanced glycolate end products and allows the RBCs to be stored under refrigeration (i.e. at between about 1 and about 6° C.) for up to 42 days (6 weeks) or longer and, and is believed to allow the RBCs to be stored for up to at least about 84 days (12 weeks) or longer, while mitigating possible negative effects of transfusing blood stored for extended periods.

The use of these compounds in an effective amount may also be beneficial in a military or humanitarian situation in which it is not possible to refrigerate the RBCs or where refrigeration is not reliable. While it may not be possible to store the treated blood for as long as in situations where it is maintained at a temperature of between about 1 and about 6° C., the use of the compounds of Structure (1) can still prevent the formation of advanced glycolate end products and allow the blood to be stored for longer periods than if the preservatives are not used.

Furthermore, the use of compounds of Structure (1) may also increase the lifespan and/or stability of RBCs in vivo and which are prone to breakdown, such as in the case of hemolytic anemia. The use of compounds of Structure (1) may be capable of halting at least some of the RBC degradation by preventing the formation of advanced glycation end products.

The compositions described herein of Structure (1) are also usable with blood substitutes incorporating RBCs to allow RBCs contained therein to live longer.

Finally, it is noted that the methods and compositions described herein are also usable for treating animal blood as well as human blood and may be used to stabilize animal blood for veterinary use, including blood of cats, dogs, horses, cows, etc. by way of example and not limitation.

What is claimed is:

1. A method of preserving red bloods cells in vitro for prolonged storage, the method comprising the steps of:
   a) adding an effective amount of the compound of Structure (1) to a unit of red blood cells that are in a first mixture with a sugar that causes the formation of advanced glycation end products:

to obtain a second mixture; and (b) storing the second mixture at a temperature between about 1 and about 6° C., wherein the presence of the compound of structure (1) in the second mixture halts the degradation of the red blood cells by preventing the formation of advanced glycation end products.

2. The method according to claim 1, wherein the effective amount of the compound of Structure (1) is an amount up to the solubility of the compound of Structure (1).

3. The method according to 1, wherein the red blood cells can be stored for up to 42 days.

4. The method according to claim 3, wherein the red blood cells can be stored for up to 84 days.

5. The method according to claim 1, wherein the red blood cells are from human blood.

6. The method according to claim 1, wherein the red blood cells are from animal blood.

7. The method according to claim 1, wherein the compound of Structure (1) reverses already formed advanced glycation end products in the red blood cells.

8. The method according to claim 1, wherein the compound of Structure (1) prevents lysis of the red blood cells.

9. A method of preserving blood-derived products in vitro for prolonged storage, the method comprising the steps of:

a) adding an effective amount of the compound of Structure (1) to a unit of a blood-derived product that is in a first mixture with a sugar that causes the formation of advanced glycation end products:

to obtain a second mixture; and (b) storing the second mixture, wherein the presence of the compound of structure (1) in the second mixture halts the degradation of the blood-derived product by preventing the formation of advanced glycation end products.

10. The method according to claim 9, wherein the blood-derived product comprises platelets.

11. The method according to claim 9, wherein the blood-derived product is stored at a temperature between about 1 and about 6° C.

* * * * *